United States Patent [19]
Plicchi et al.

[11] Patent Number: 5,501,702
[45] Date of Patent: Mar. 26, 1996

[54] TIME SHARING MULTIPOLAR RHEOGRAPHY APPARATUS AND METHOD

[75] Inventors: Gianni Plicchi, Bologna; Massimo Ceccarelli, Cesena, both of Italy

[73] Assignee: Medtronic, Inc., Minneapolis, Minn.

[21] Appl. No.: 277,051

[22] Filed: Jul. 19, 1994

[30] Foreign Application Priority Data

Jun. 6, 1994 [IT] Italy .................. RM94A0356

[51] Int. Cl.⁶ ............................................. A61N 1/36
[52] U.S. Cl. .................................................. 607/20
[58] Field of Search .................... 607/17, 20, 24, 607/5

[56] References Cited

U.S. PATENT DOCUMENTS

4,485,813  12/1984  Anderson .
4,702,253  10/1987  Nappholz .
4,721,110   1/1988  Lampadius .
5,052,388  10/1991  Sivula .

Primary Examiner—William E. Kamm
Assistant Examiner—Scott M. Getzow
Attorney, Agent, or Firm—Michael J. Jaro; Harold R. Patton

[57] ABSTRACT

A cardiac pacemaker having switching circuitry for dynamically re-assigning the electrical function of a plurality of electrodes coupled thereto. The pacemaker is provided with switching circuitry for allowing the sensing signals from a plurality of implanted electrodes may be selectively applied to sensing and detection circuitry in the pacemaker. Controller circuitry in the pacemaker controls the operation of the switching circuits and of a rheography current pulse generator such that a plurality of time slots are defined during a sensing interval. During successive time slots, a different electrical function may be assigned to the same electrode. Also disclosed is a method of operating such a pacing system.

7 Claims, 10 Drawing Sheets

TIME SHARING MULTIPOLAR RHEOGRAPHY APPARATUS AND METHOD

FIELD OF THE INVENTION

This invention relates to the field of implantable medical devices, and more particularly relates to implantable cardiac devices such as pacemakers, defibrillators, and the like.

BACKGROUND OF THE INVENTION

A wide variety of cardiac pacemakers are known and commercially available. Pacemakers are generally characterized by which chambers of the heart they are capable of electrically sensing, the chambers to which they deliver pacing stimuli, and their ability to respond, in their operation, to indicia of normal or abnormal cardiac functioning. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiologically-based signals, such as signals from sensors for measuring the pressure inside the patient's ventricle or for measuring the level of the patient's physical activity. In recent years, pacemakers which measure the metabolic demand for oxygen and vary the pacing rate in response thereto have become available. Perhaps the most popularly employed method for measuring the need for oxygenated blood is to measure the physical activity of the patient by means of a piezoelectric transducer. Such a pacemaker is disclosed in U.S. Pat. No. 4,485,813 issued to Anderson et al.

In typical prior art rate-responsive pacemakers, the pacing rate is determined according to the output from an activity sensor. The pacing rate is variable between a predetermined maximum and minimum level, which may be selectable by a physician from among a plurality of programmable upper and lower rate limit settings. When the activity sensor output indicates that the patient's activity level has increased, the pacing rate is increased from the programmed lower rate by an incremental amount which is determined as a function of the output of the activity sensor. That is, the rate-responsive or "target" pacing rate in a rate-responsive pacemaker is determined as follows:

Target Rate=Programmed Lower Rate+f(sensor output)
where f is typically a linear or monotonic function of the sensor output. As long as patient activity continues to be indicated, the pacing rate is periodically increased by incremental amounts calculated according to the above formula, until the programmed upper rate limit is reached. When patient activity ceases, the pacing rate is gradually reduced, until the programmed lower rate limit is reached.

In an effort to minimize patient problems and to prolong or extend the useful life of an implanted pacemaker, it has become common practice to provide numerous programmable parameters in order to permit the physician to select and/or periodically adjust the desired parameters or to match or optimize the pacing system to the patient's physiologic requirements. The physician may adjust the output energy settings to maximize pacemaker battery longevity while ensuring an adequate patient safety margin. Additionally, the physician may adjust the sensing threshold to ensure adequate sensing of intrinsic depolarization of cardiac tissue, while preventing oversensing of unwanted events such as myopotential interference or electromagnetic interference (EMI). Also, programmable parameters are typically required to enable and to optimize a pacemaker rate response function. For example, Medtronic, Inc.'s Legend and Activitrax series of pacemakers are multiprogrammable, rate-responsive pacemakers having the following programmable parameters: pacing mode, sensitivity, refractory period, pulse amplitude, pulse width, lower and upper rate limits, rate response gain, and activity threshold.

For any of the known rate-responsive pacemakers, it is clearly desirable that the sensor output correlate to as high a degree as possible with the actual metabolic and physiologic needs of the patient, so that the resulting rate-responsive pacing rate may be adjusted to appropriate levels. A piezoelectric activity sensor can only be used to indirectly determine the metabolic need. The physical activity sensed can be influenced by upper body motion. Therefore, an exercise that involves arm motion may provide signals that are inappropriately greater than the metabolic need. Conversely, exercises that stimulate the lower body only, such as bicycle riding, may provide a low indication of metabolic need while the actual requirement is very high. Therefore, it would be desirable to implement a rate-responsive pacemaker that is based on a parameter that is correlated directly to metabolic need.

Minute ventilation ($V_e$) has been demonstrated clinically to be a parameter that correlates directly to the actual metabolic and physiologic needs of the patient. Minute ventilation is defined by the equation:

$$V_e = RR \times VT$$

where RR=respiration rate in breaths per minute (bpm), and VT=tidal volume in liters. Clinically, the measurement of $V_e$ is performed by having the patient breathe directly into a device that measures the exchange of air and computes the total volume per minute. The direct measurement of $V_e$ is not possible with an implanted device. However, $V_e$ can indirectly measured by monitoring impedance changes in the patient's thoracic cavity. Such impedance measurements can be performed with implantable circuitry and implantable leads.

In general, the measurement of the impedance present between two or more sensing locations is referred to as rheography. Typically, rheographic measurement involves delivering a constant current pulse between two "source" electrodes, such that the current is conducted through some region of a patient's tissue, and then measuring the voltage differential between two "recording" electrodes to ascertain the impedance of the tissue, the voltage differential arising from the conduction of the current pulse through the tissue.

A pacemaker with rheographic capabilities can measure thoracic impedance in a patient by delivering a known current between two of the pacemaker's electrodes. A pacemaker capable of measuring thoracic impedance with rheography is disclosed in U.S. Pat. No. 4,702,253 issued to Nappholz et al. on Oct. 27, 1987; the Nappholz et al. patent is hereby incorporated by reference herein in its entirety. In the Nappholz arrangement, the magnitude of the change of the impedance signal corresponds to the tidal volume and the frequency of change corresponds to respiration rate.

In U.S. Pat. No. 4,721,110 issued to Lampadius on Jan. 26, 1988, there is described a rheographic arrangement for a cardiac pacemaker in which the base pacing rate of the pacemaker is determined, in part, by a rheographically-obtained respiration rate signal. According to the Lampadius patent, rheographic current pulses can interfere with the sensing of electrical cardiac signals, and are therefore delivered only during the refractory period immediately preceding delivery of a stimulating pulse.

There continues to be a wide interest among implantable pulse generator manufacturers in using rheographic techniques to measure such physiological parameters as minute ventilation. This is due in part to the fact that rheographic techniques allow measurement of physiological parameters without the need for a special sensor (such as the piezoelectric sensor on the canister of activity-sensing pacemakers). Rheographic techniques require, at most, the use of multiple electrodes located on a standard pacing lead.

There are currently several commercially available implantable devices which employ rheographic techniques to adjust the pacing rate according to metabolic needs. For example, the Biorate device manufactured by Biotec International, Bologna Italy, uses a bipolar (i.e., two-electrode configuration) rheographic arrangement to monitor the patient's respiratory rate. The Meta-MV device manufactured by Telectronics, Inc., Englewood, Colo., uses a tripolar rheographic arrangement to monitor the patient's respiratory rate. The Precept device manufactured by CPI, St. Paul, Minn., uses a tetrapolar rheographic arrangement to monitor the patient's pre-ejection interval (PEI), stroke volume (SV), and heart tissue contractility. It is well known that other manufacturers are exploring or have explored the use of rheographic techniques to monitor physiological parameters.

The parameters measured by rheography in presently known devices are essentially derived from two sources: respiration and cardiac systole. Respiration is typically measured with either a bipolar configuration in which the pacemaker's conductive canister and a large surface area electrode are used, or with a tripolar configuration using standard pacing/sensing leads having much smaller surface area electrodes. With configurations using small surface area leads, the source and recording functions must be kept spaced apart, to avoid detection of contact resistance variations. Signals representative of respiratory rate, tidal volume, and minute ventilation can be derived using bipolar or tripolar configurations.

Detection of cardiac systole, on the other hand, is currently believed to require a tetrapolar configuration. Pre-ejection interval, stroke volume, and contractility can be derived from a tetrapolar rheographic configuration.

Attempts have been made and described in the literature to utilize bipolar rheographic configurations (e.g., Tip-to-Can or Tip-to-Ring sensing configurations), with standard pacing/sensing leads, to detect both respiration and systole. However, such methods do not appear to lead to a useful result, since only multipolar techniques achieve consistent impedance measurement using small surface area electrodes.

It has been the inventors' experience that bipolar rheographic configurations, which derive a signal that is a composite of cardiac systole effects and respiration effects, are highly susceptible to variations in the contact resistance of the electrodes. The contact resistance varies because respiration and cardiac systole induce a deformation on the pacing/sensing lead, thus changing the pressure of the tip electrode on the myocardial tissue. Screw-in leads reduce, but do not eliminate, the inconsistency in bipolar rheographic measurement.

Thus, it is believed that different electrode configurations are required to detect both respiration and cardiac systole. That is, both the position and the function of the electrodes must be different depending upon whether cardiac systole or respiration is to be measured.

A further consideration in the selection of an electrode configuration for a pacemaker is the necessity of accurate sensing of cardiac electrical signals, including those associated with atrial contractions (i.e., "P-waves"), and those associated with ventricular contractions ("R-waves" or "QRS complexes"). Atrial sensing is especially difficult, due to the low magnitude of P-waves in relation to R-waves and the resulting problems of discriminating P-waves from R-waves. With only a single atrial electrode, the atrial signal (P-wave) detected by the atrial electrode is very similar to the ventricular signal (R-wave) appearing at that same electrode. Mere amplification of the atrial signal, therefore, does not assist in discriminating atrial from ventricular signals detected in the atrium, or in discriminating atrial signals from myopotentials or external interference.

The use of more than one atrial electrode has proven to be useful in atrial signal discrimination. This is because two atrial electrodes placed at different locations in the atrium will detect similar ventricular signals but atrial signals that are different in both amplitude and morphology.

In conventional pacemaker systems, the electrode configuration is fixed, such that a specific function is assigned to each electrode (the electrode placement, of course, also being fixed). For example, in the above-noted Telectronics Meta-MV device, the tip electrode of the bipolar pacing/sensing lead is always "recording" (i.e., receiving current), the ring electrode of the lead is always the "source" (i.e., producing a current); and the conductive pacemaker canister is always a source and recording electrode. This configuration allows measurement of impedance variation primarily due to respiration.

In the CPI Precept device, the tip electrode is always the "source" the canister is also always the "source" and two ring electrodes on the pacing lead proximal to the tip electrode, are always "recording". This configuration allows measurement of impedance variation primarily due to cardiac systole.

There has yet to be shown in the art, however, an implantable device capable of dynamically adapting its electrode configuration for the purposes of obtaining different physiological measurements.

SUMMARY OF THE INVENTION

It is a feature of the present invention, therefore, that an implantable cardiac stimulating device is provided with circuitry for dynamically adapting its electrode configuration so that the same electrode can serve different functions at different times.

It is another feature of the present invention that a pacemaker is provided which is capable of reassigning the electrical function of a plurality of implanted electrodes such that multiple sensing configurations may be realized with a plurality of physically fixed electrodes.

It is still another feature of the invention that a pacemaker is provided which is capable of performing a plurality of different sensing operations on a time-sharing basis.

In accordance with the present invention, switching circuitry is provided with switching circuitry for allowing the sensing signals from a plurality of implanted electrodes may be selectively applied to sensing and detection circuitry in the pacemaker. Controller circuitry in the pacemaker controls the operation of the switching circuits and of a rheography current pulse generator such that a plurality of time slots are defined during a sensing interval. During successive time slots, a different electrical function may be assigned to the same electrode.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF THE INVENTION

Figure 1:
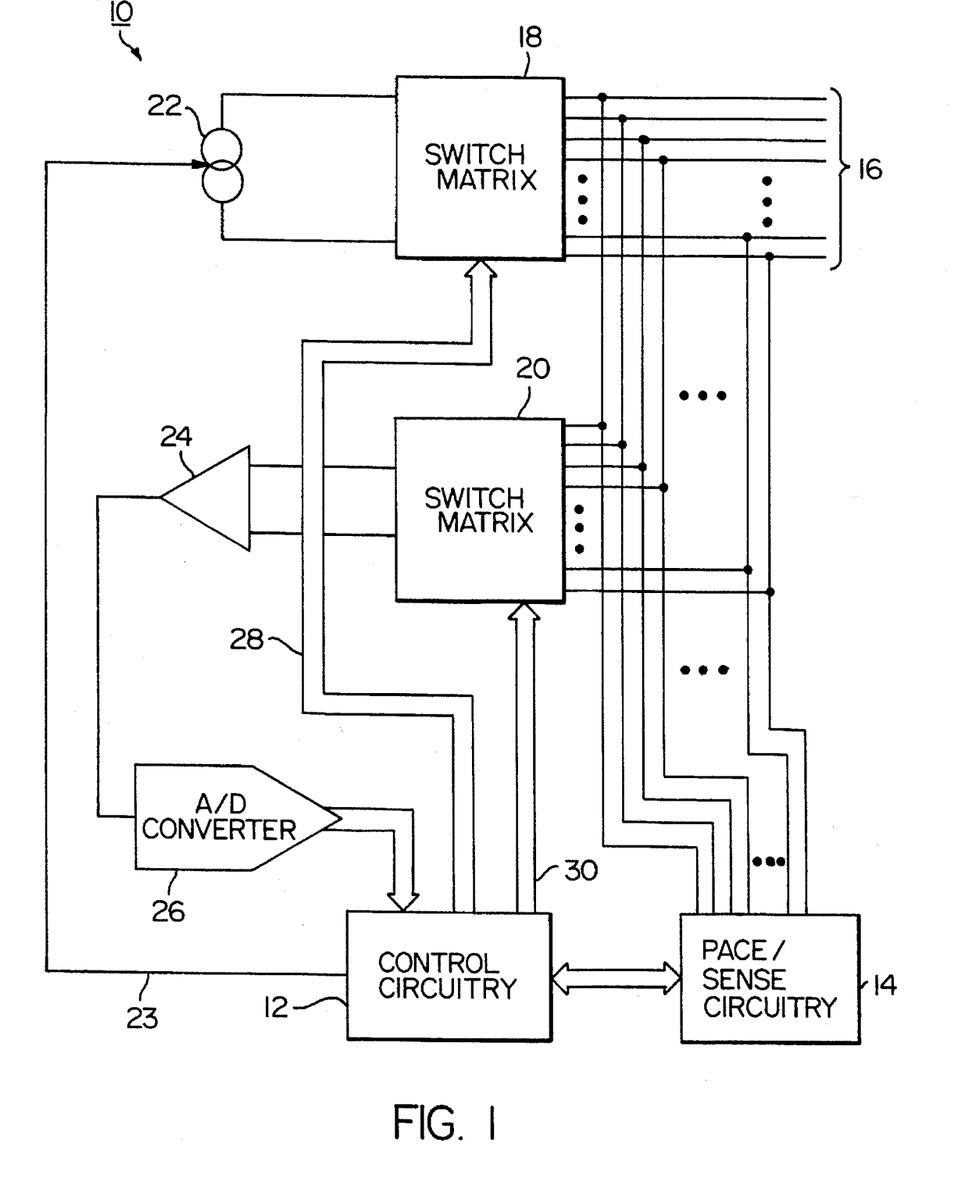
FIG. 1 is a block diagram of a pacemaker in accordance with one embodiment of the present invention.

Referring to FIG. 1, there is shown a simplified block diagram of an implantable cardiac pacemaker 10 in accordance with one embodiment of the present invention. Pacemaker 10 operates under control of control circuitry 12 which may include a microprocessor or custom integrated circuitry, as would be appreciated by those of ordinary skill in the art. Control circuitry 12 is coupled to pace/sense circuitry 14 such that pace/sense circuitry 14 can provide signals to control circuitry 12 indicating the detection of electrical cardiac events (P-waves, R-waves, and the like), and such that control circuitry 12 can provide triggering signals to pace/sense circuitry 14 to initiate delivery of cardiac stimulating pulses. To the extent that control circuitry 12 and pace/sense circuitry 14 operate to detect cardiac events and deliver cardiac stimulating pulses, these circuits are of conventional and well-known design and will not be described herein in further detail. It is believed that those of ordinary skill in the art would be familiar with the design and operation of pacemaker control circuitry and pace/sense circuitry such as is included in pacemaker 10 in accordance with the presently disclosed embodiment of the invention.

Control circuitry and pace/sense circuitry suitable for use in the practice of the present invention is described in some detail in U.S. Pat. No. 5,052,388 to Sivula et al., which patent is owned by the assignee of the present invention and is hereby incorporated by reference herein in its entirety. It is believed, however, that any of the well-known and commercially-available pacemakers may be readily adapted in accordance with the present invention by those of ordinary skill in the art having the benefit of the present disclosure.

As shown in FIG. 1, pace/sense circuitry 14 is coupled to a plurality of lead conductors designated collectively in FIG. 1 by reference numeral 16. It is to be understood that the connection between lead conductors 16 and pace/sense circuitry 14 can be implemented using any of the well-known lead connection arrangements. For example, lead conductors 16 disposed in one or more implantable pace/sense leads can be coupled to circuitry internal to pacemaker 10 by means of a conventional lead connector block disposed on the pacemaker canister. The details of connections between implantable leads and the circuitry of pacemaker 10 will not be described herein in detail, as it is believed that the manner of making such connections is well known can be readily implemented by those of ordinary skill in the art.

Lead conductors 16 are also coupled in the pacemaker 10 of FIG. 1 to a first switch matrix 18 and a second switch matrix 20. As will hereinafter be described in greater detail, switch matrix 18 establishes a selectable interconnection between particular ones of lead conductors 16 and a current source 22, for the purpose of delivering rheography pulses on lead conductors 16. In a similar manner, switch matrix 20 establishes a selectable interconnection between particular ones of lead conductors 16 and an impedance detection circuit 24, for the purpose of receiving rheography pulses from lead conductors 16.

As shown in FIG. 1, current source 22 receives at least one control signal on line 23 issued from control circuitry 12. Current source 22 is responsive to control signals issued by control circuitry 12 to deliver constant current rheography pulses onto lead conductors 16. As will hereinafter be described in greater detail, switching matrix 18 functions to determine which of the lead conductors 16 will receive the rheography current pulses generated by current source 22. The details of implementation of current source 22 are not critical to an understanding of the present invention, and it is believed that those of ordinary skill in the circuit art would be able to implement current source 22 in various ways suitable for the purposes of the present invention.

Impedance detection circuit 24 is adapted to monitor the voltage between pairs of electrodes to which it is selectively coupled by operation of switch matrix 20, in order to determine the voltage (and hence the impedance) existing between the two electrodes. As would be appreciated by those familiar with rheographic techniques, such impedance measurement can provide an indication of various physiological events, including cardiac systole and respiratory cycles, as previously discussed. In the presently preferred embodiment of the invention, impedance detection circuit 24 is a differential amplifier, the implementation of which would be a matter of routine to those of ordinary skill in the circuit art.

An analog-to-digital converter (ADC) 26 is coupled to the output of impedance detection circuit 24. Impedance circuit 24 produces an impedance output voltage that is proportional to the impedance between a selected pair of lead electrodes. ADC 26, in turn, produces a multiple-bit digital value corresponding to the analog impedance circuit output voltage. The digital impedance value is then provided to control circuit 12. It is believed that any of the various well-known and commercially available ADCs would be suitable for use in the practice of the present invention, and that no detailed description of the design and operation of ADC 26 is necessary herein.

Figure 2:
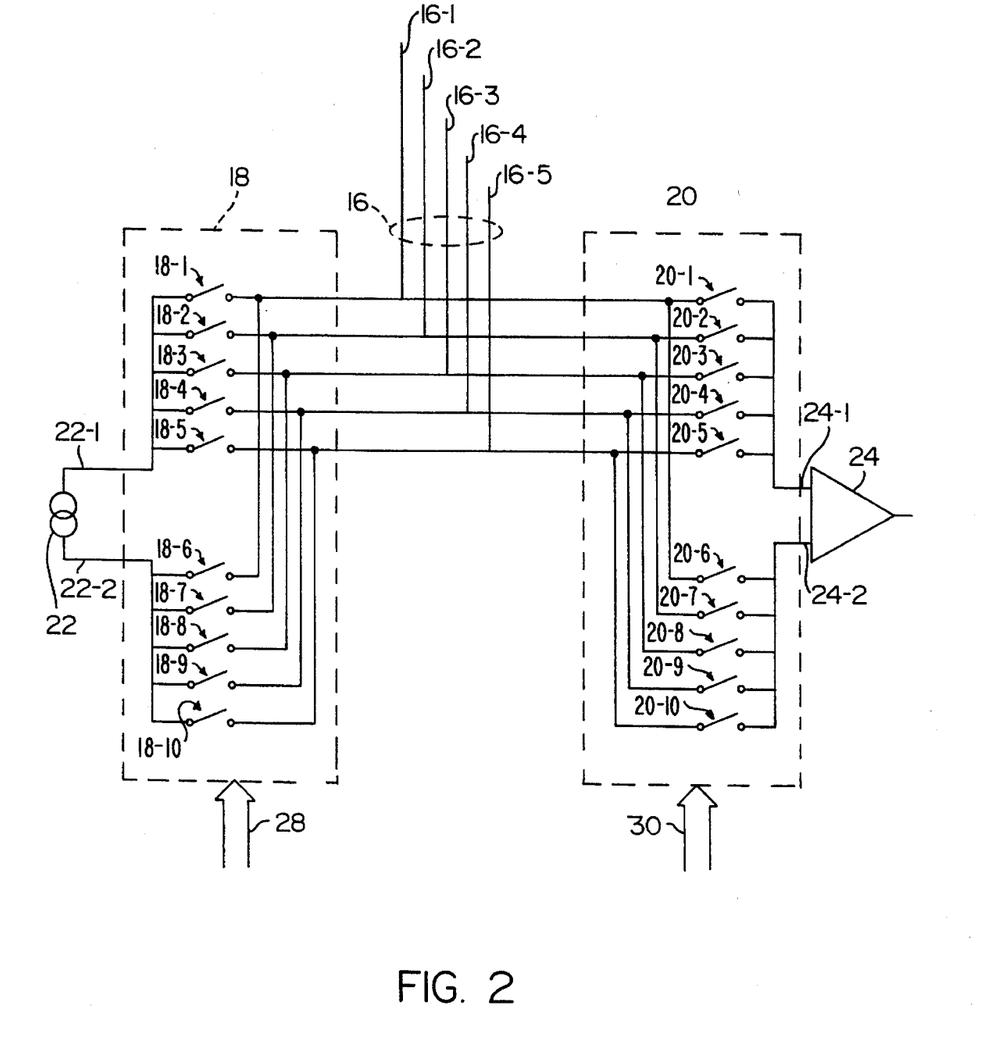
FIG. 2 is a schematic diagram of the switch matrices, current source, and impedance detection circuit from the pacemaker of FIG. 1.

Turning now to FIG. 2, there is shown a more detailed schematic diagram of switching circuits 18 and 20 and the interconnection of those circuits to rheographic current source 22 and impedance detection circuit 24. In FIG. 2, there are five lead conductors 16, which are individually designated in FIG. 2 as 16-1 through 16-5. Each of the lead conductors 16 is coupled to a different electrode disposed in a sensing relationship. For example, and in the embodiment of FIG. 2, lead conductors 16-4 and 16-5 are coupled to separate ventricular electrodes on an implanted pacing/sensing lead, conductors 16-2 and 16-3 are coupled to atrial electrodes on an implanted lead, and conductor 16-1 is coupled to the conductive pacemaker canister.

Switching circuit 18 comprises a plurality of individual switches 18-1 through 18-10. Switches 18-1 through 18-5 selectively couple lead conductors 16-1 through 16-5, respectively, to a first input terminal 22-1 of current source 22. Switches 18-6 through 18-10 selectively couple lead conductors 16-1 through 16-5, respectively, to a second input terminal 22-2 of current source 22.

Similarly, switching circuit 20 comprises a plurality of switches 20-1 through 20-10. Switches 20-1 through 20-5 selectively couple lead conductors 16-1 through 16-5, respectively, to a first input terminal 24-1 of impedance detection circuit 24. Switches 20-6 through 20-10 selectively couple lead conductors 16-1 through 16-5, respectively, to a second input terminal 24-2 of impedance detection circuit 24.

As would be apparent to those of ordinary skill in the art, the configuration of switching circuits 18 and 20 in FIG. 2 allows any one or more lead conductors 16 to function as a "source" of rheography current pulses. That is, any two lead conductors 16 can, with an appropriate activation of switches 18-1 through 18-10, be coupled to current source 22. Furthermore, the arrangement shown in FIG. 2 allows any one or more lead conductors 16 to "record" (i.e., receive) the rheography current pulses. That is, any two lead conductors 16 can, with an appropriate activation of switches 20-1 through 20-10, be coupled to impedance detection circuit 24.

In the presently preferred embodiment of the invention, switches 18-1 through 18-10, and switches 20-1 through 20-10 are implemented as field-effect transistor (FET) switches which are independently actuated by gate control signals produced by control circuitry 12. With reference to FIG. 1, the control signals for switch matrix 18 are conducted from control circuitry 12 on a plurality of control signal lines 28, while control signals for switch matrix 20 are conducted from control circuitry 12 on a plurality of control signal lines 30. Although FET switches are presently believed to be preferred, it is contemplated that many other types of switching mechanisms may be employed in practicing the present invention.

In accordance with another underlying feature of the present invention, the rheography circuitry of pacemaker 10 is capable of operating in a multi-polar time-sharing mode wherein a plurality of rheographic pulses are generated in sequence, with the configuration of source and recording electrodes being different for each pulse delivered. The period of time during which rheographic measurements are to be taken (e.g., the refractory period preceding delivery of a stimulating pulse, as discussed in the aforementioned Lampadius patent) is conceptually divided into a series of "time slots". Switches 18 and 20 are operated in timed synchronism with the delivery of a sequence of rheographic current pulses from current source 22 such that a rheographic pulse is delivered to a different source/recording electrode configuration during each time slot. Such operation of the rheography circuitry in pacemaker 10 will be better appreciated with reference to some specific example configurations to be hereinafter described.

In the presently preferred embodiment of the invention, time slots of between 0.01 to 100-Msec or so duration may be defined. During each time slot, the state of switches 18 and 20 determine what type of rheographic measurement is to be taken. It is believed that the length of time slots can vary from implementation to implementation.

EXAMPLE NO. 1

Figure 3:
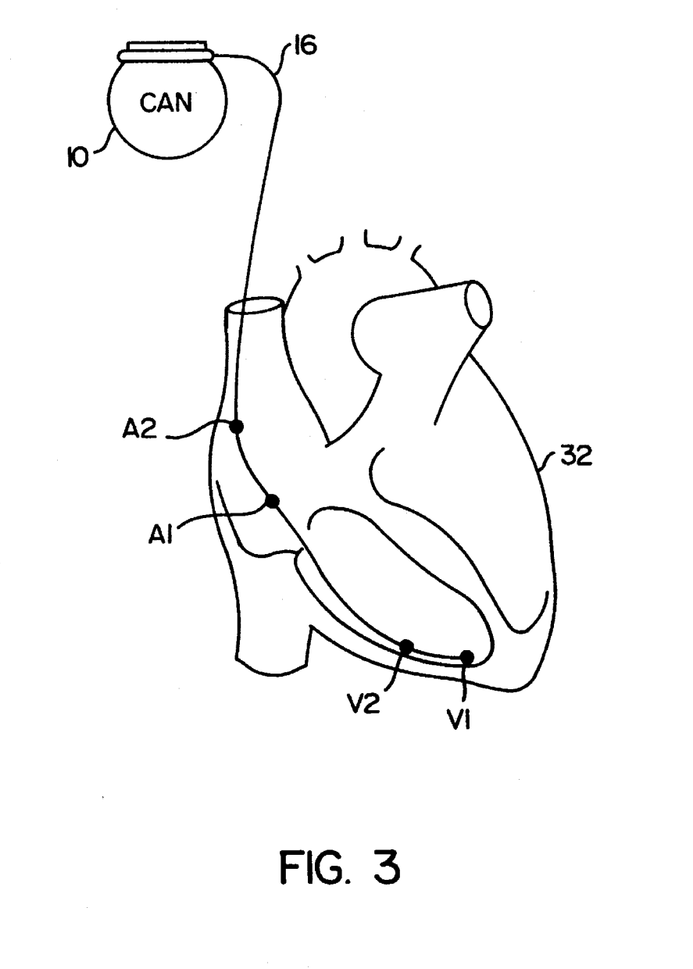
FIG. 3 is a diagram illustrating one lead configuration for the pacemaker of FIG. 1.

With reference now to FIG. 3, a particular configuration of pacemaker 10 is depicted. In FIG. 3, pacemaker 10 and lead 16 are shown in relation to a patient's heart 32. In the configuration depicted in FIG. 3, lead 16 is a standard quadripolar lead having, as shown, two atrial ring electrodes A1 and A2 and two ventricular electrodes V1 and V2. As would be appreciated by those of ordinary skill in the pacing art, such a lead configuration is a conventional one for pacing in the VDD pacing mode, with bipolar ventricular sensing.

With the configuration of FIG. 3, it is possible to perform five-pole rheographic measurement during a rheographic sequence consisting of four separate time slots. The configuration of source and recording electrodes during the four time slots of the rheography sequence is set forth in the following Table 1. For each entry in Table 1 (and each of the tables to follow), an "S" indicates that the electrode corresponding to that entry functions as a "source" during the time slot corresponding to that entry. An "R" entry indicates that the electrode corresponding to that entry functions as a "recording" electrode during the corresponding time slot. An entry of "--" indicates that electrode corresponding to that entry is not involved in the rheographic measurement during the corresponding time slot.

TABLE 1

|  | TIME SLOT 1-0 | TIME SLOT 1-1 | TIME SLOT 1-2 | TIME SLOT 1-3 |
|---|---|---|---|---|
| CAN | S/R | S/R | S | — |
| A2 | R | — | R | S |
| A1 | S | — | R | R |
| V2 | — | S | S | S |
| V1 | — | R | — | R |

As indicated in Table 1, during Time Slot 1-0, the pacemaker canister serves as both a source and recording electrode; atrial electrode A2 serves as a recording electrode, and atrial electrode A1 serves as a source electrode. In this example, the correspondence between the electrodes and the lead conductors shown in FIG. 2 is assumed to be as set forth in the following Table 2:

TABLE 2

| LEAD CONDUCTOR | ASSOCIATED ELECTRODE |
|---|---|
| 16-1 | CANISTER |
| 16-2 | A2 |
| 16-3 | A1 |
| 16-4 | V2 |
| 16-5 | V1 |

Figure 4:
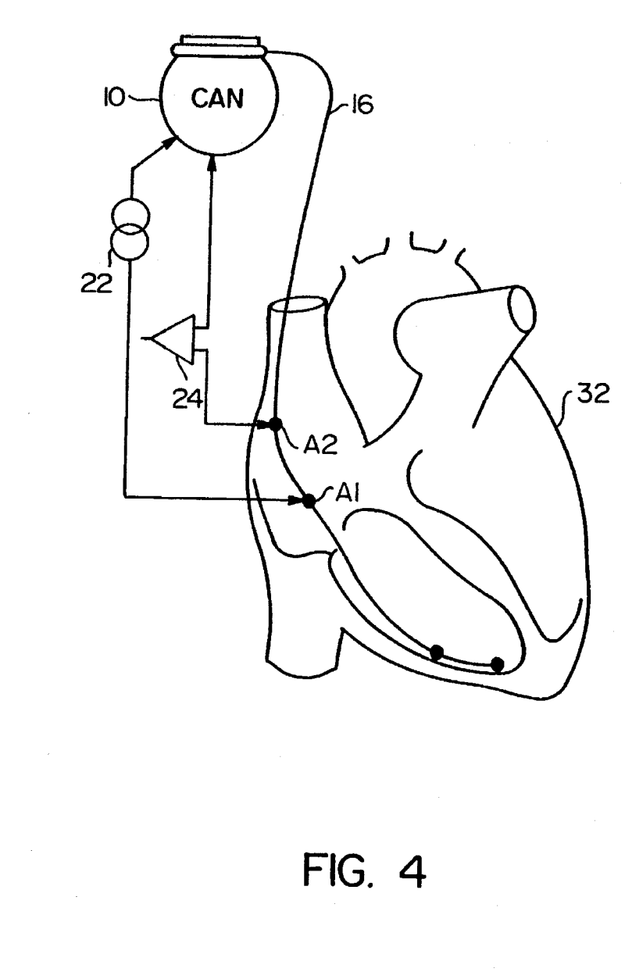
FIGS. 4, 5, 6, and 7 are diagrams illustrating four rheographic measurement configurations available with the lead configuration of FIG. 3.

Thus, the configuration during Time Slot 1-0 is realized by closing switches 18-1 and 18-8, as well as switches 20-1 and 20-7, leaving all other switches open. This results in the arrangement shown in FIG. 4, wherein it can be seen that current source 22 is coupled to the pacemaker canister and to atrial electrode A1, while impedance detection circuit 24 is coupled to the pacemaker canister and to atrial electrode A2. Thus, during Time Slot 1-0, transthoracic impedance (i.e., ventilation) is measured.

Figure 5:
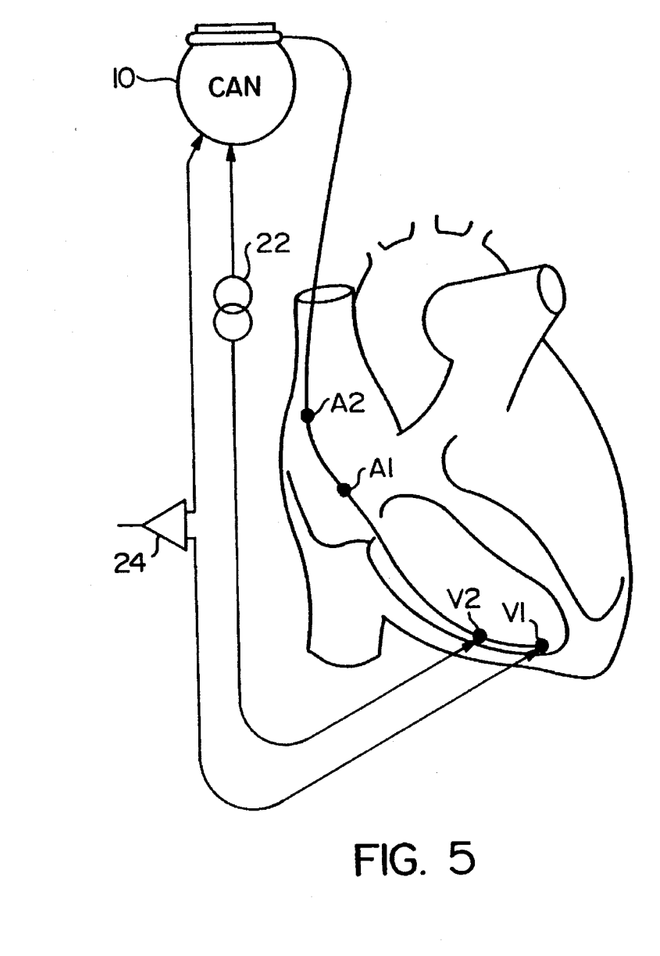

During Time Slot 1-1, the pacemaker canister again serves as both a recording and source electrode. Ventricular electrode V2 serves as a source electrode, and ventricular electrode V1 serves as a recording electrode. This is achieved by closing switches 18-1 and 18-9, along with switches 20-1 and 20-10, again leaving all other switches open. The effective configuration of Time Slot 1-1 is shown in FIG. 5. Current source 22 is coupled to the pacemaker canister and to electrode V2, while impedance detection circuit 24 is coupled to the pacemaker canister and to ventricular electrode V1. During Time Slot 1-1, transthoracic impedance is measured using the tripolar configuration used by the aforementioned Telectronics Meta-MV pacemaker.

Figure 6:
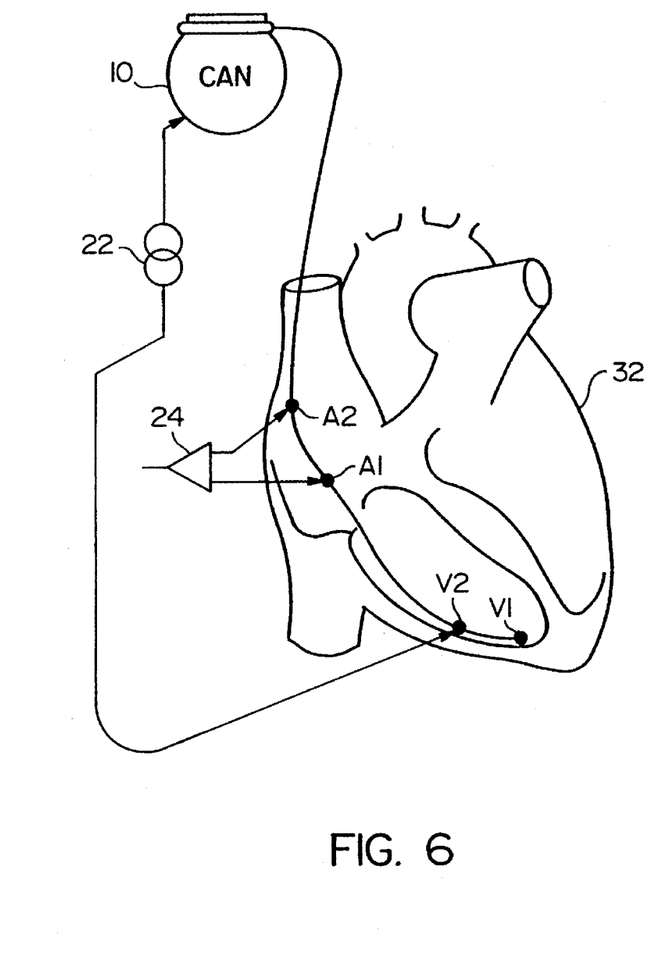

During Time Slot 1-2, the pacemaker canister and ventricular electrode V2 serve as source electrodes, while the two atrial electrodes A1 and A2 serve as recording electrodes. This configuration, realized by closing switches 18-1 and 18-9, as well as switches 20-2 and 20-8, is depicted in FIG. 6. During Time Slot 1-2, atrial intracardiac impedance is measured.

Figure 7:
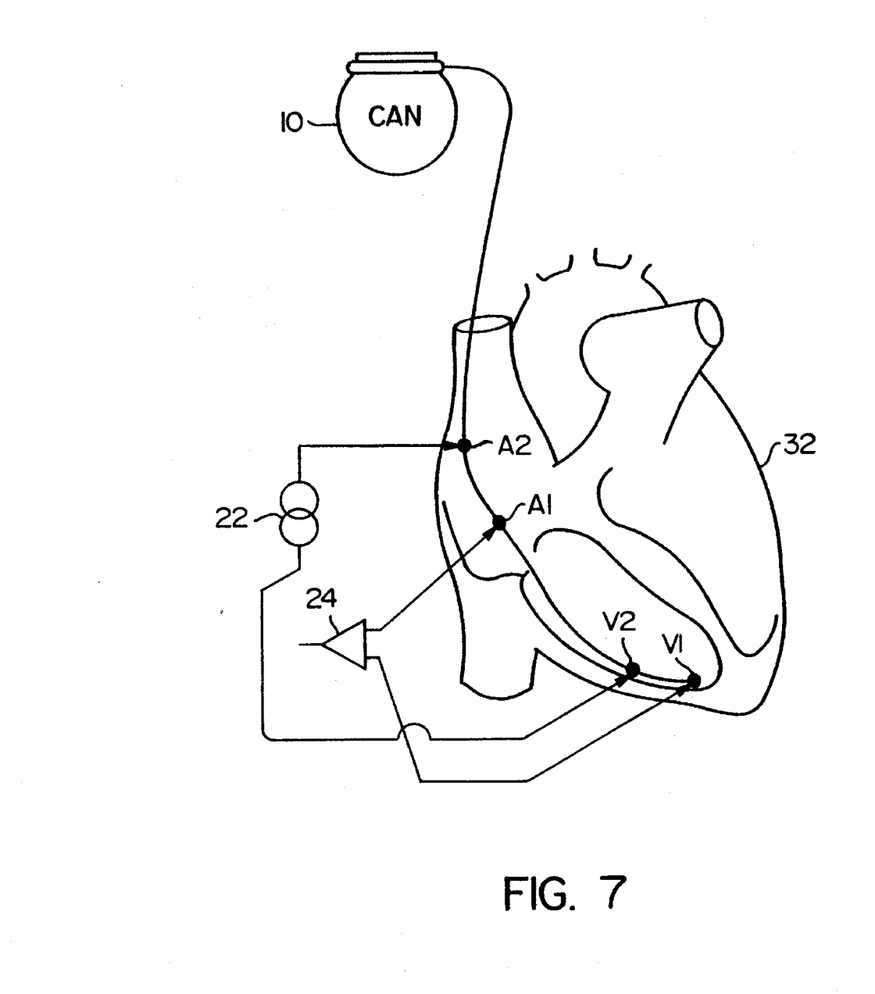

During Time Slot 1-3, atrial electrode A2 and ventricular electrode V2 serve as source electrodes, while atrial electrode A1 and ventricular electrode V1 serve as recording electrodes. This configuration, realized by closing switches 18-2 and 18-9, along with switches 20-3 and 20-10, is depicted in FIG. 7. During Time Slot 1-3, ventricular intracardiac impedance is measured.

EXAMPLE NO. 2

Figure 8:
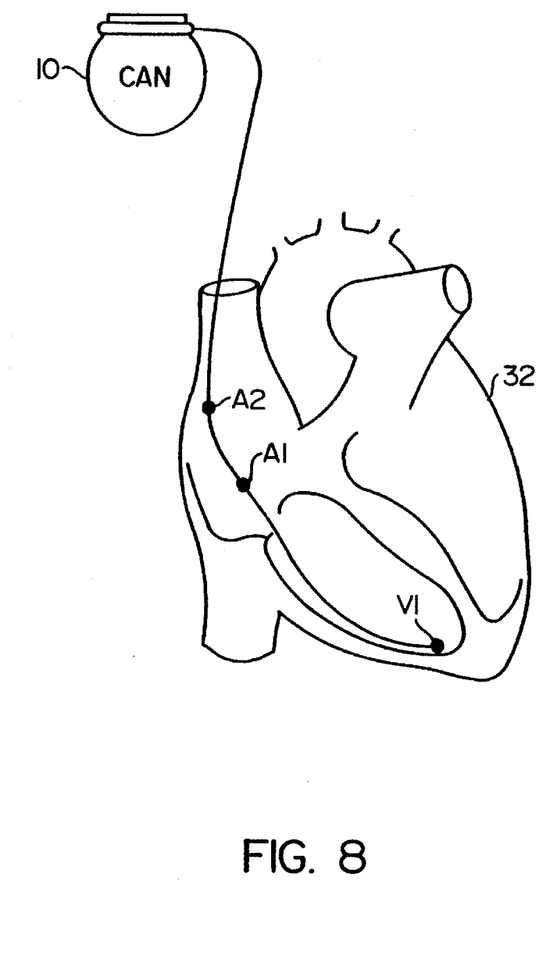
FIG. 8 is a diagram illustrating a second lead configuration for the pacemaker of FIG. 1.

Turning now to FIG. 8, there is shown a second example configuration which utilizes a standard tripolar lead having two atrial electrodes and one ventricular electrode. As would be appreciated by those of ordinary skill in the pacing art, the configuration of FIG. 8 is a conventional one for performing VDD pacing with unipolar ventricular sensing.

With the configuration of FIG. 8, it is possible to perform quadripolar rheographic measurement in two time slots. The configuration during the two time slots is set forth in the following Table 3:

TABLE 3

|  | TIME SLOT 2-0 | TIME SLOT 2-1 |
|---|---|---|
| CAN | S/R | S |
| A2 | R | R |
| A1 | S | R |
| V1 | — | S |

In this second example configuration, the correspondence between lead conductors identified in FIG. 2 and the electrodes and canister is assumed to be as set forth in the following Table 4:

TABLE 4

| LEAD CONDUCTOR | ASSOCIATED ELECTRODE |
|---|---|
| 16-1 | CANISTER |
| 16-2 | A2 |
| 16-3 | A1 |
| 16-4 | NONE |
| 16-5 | V1 |

Figure 9:
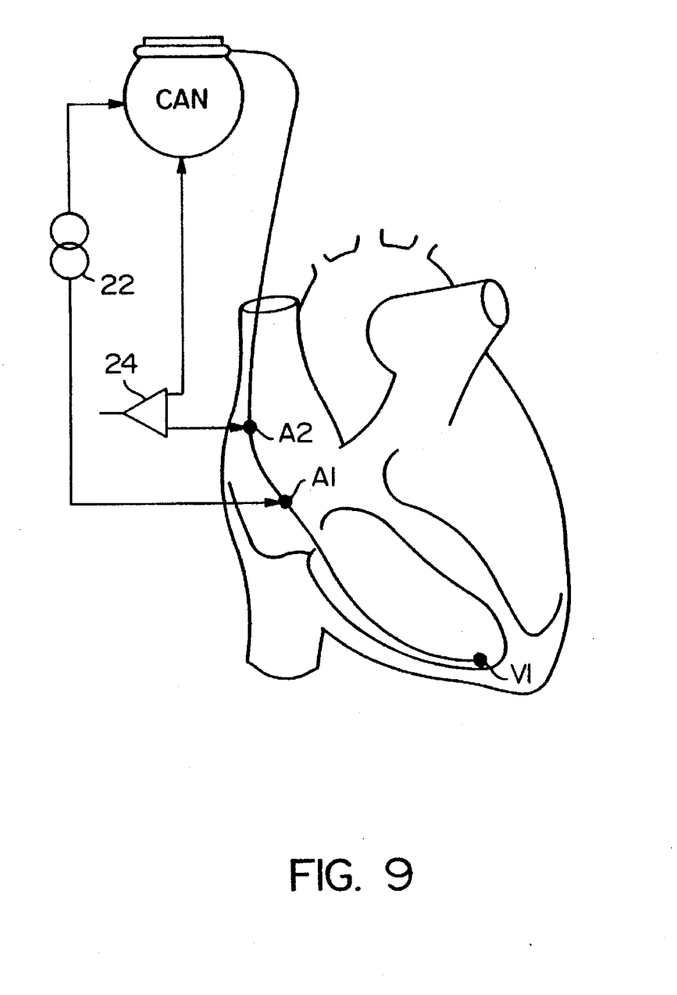
FIGS. 9 and 10 are diagrams illustrating two rheographic measurement configurations available with the lead configuration of FIG. 8.

In Time Slot 2-0, the pacemaker canister functions as both a source and a recording electrode. Atrial electrode A2 serves as a recording electrode, and atrial electrode A1 serves as a source electrode. This configuration, achieved by closing switches 18-1 and 18-8 and switches 20-1 and 20-7, is depicted in FIG. 9. During Time Slot 2-0, transthoracic impedance is measured.

Figure 10:
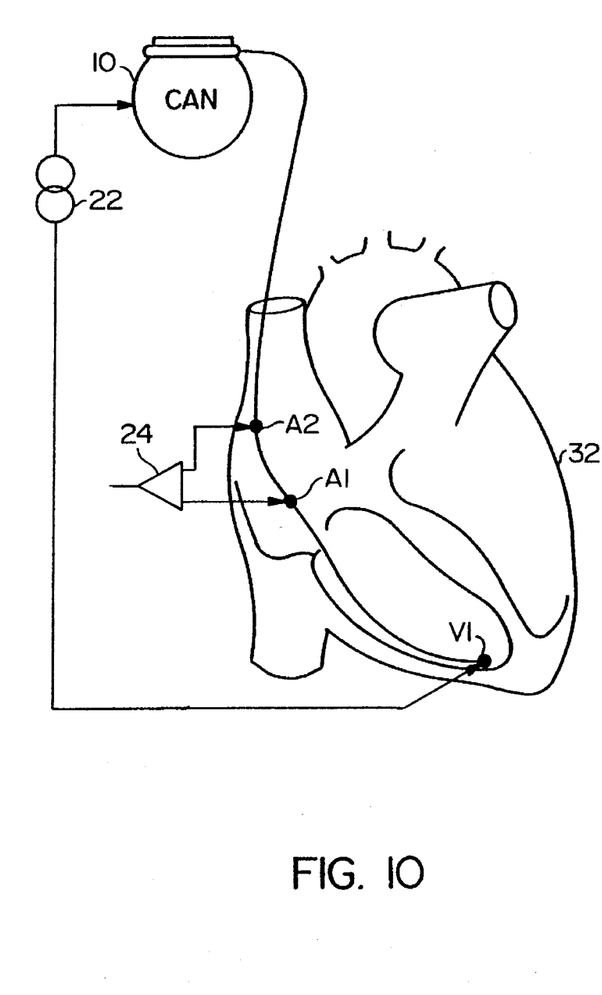

In Time Slot 2-1, the pacemaker canister and ventricular electrode V1 serve as source electrodes, while the two atrial electrodes A2 and A1 serve as recording electrodes. This is accomplished by closing switches 18-1 and 18-10, along with switches 20-2 and 20-8. (It is to be understood that since there is only a single ventricular electrode in the example configuration of FIG. 8, switches 18-4, 18-9, 20-4, and 20-9 associated with the second ventricular electrode (see FIG. 2) are not used.) The configuration corresponding to Time Slot 2-1 is depicted in FIG. 10. With this configuration, atrial transthoracic impedance is measured.

EXAMPLE NO. 3

Figure 11:
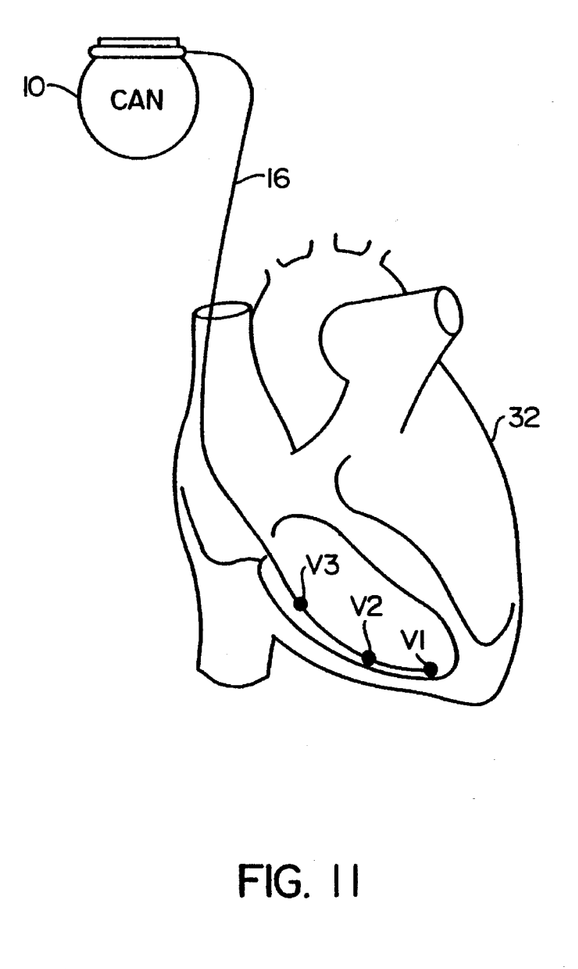
FIG. 11 is a diagram illustrating a third lead configuration for the pacemaker of FIG. 1.

In FIG. 11, there is shown a third example configuration of pacemaker 10 in accordance with the presently disclosed embodiment of the invention. In the configuration of FIG. 11, a standard tripolar lead is used. This arrangement is suitable for performing VVI pacing with tripolar ventricular sensing. This arrangement also allows for quadripolar rheographic measurement in two time slots. The two time slots are defined for the configuration of FIG. 11 as set forth in the following Table 5:

TABLE 5

|  | TIME SLOT 3-0 | TIME SLOT 3-1 |
|---|---|---|
| CAN | S/R | S |
| V3 | R | R |
| V2 | S | R |
| V1 | — | S |

In this third example, the correspondence between lead conductors 16-1 through 16-5 in FIG. 2 and the ventricular electrodes and canister is assumed to be as set forth in the following Table 6:

TABLE 6

| LEAD CONDUCTOR | ASSOCIATED ELECTRODE |
|---|---|
| 16-1 | CANISTER |
| 16-2 | NONE |
| 16-3 | V3 |
| 16-4 | V2 |
| 16-5 | V1 |

Figure 12:
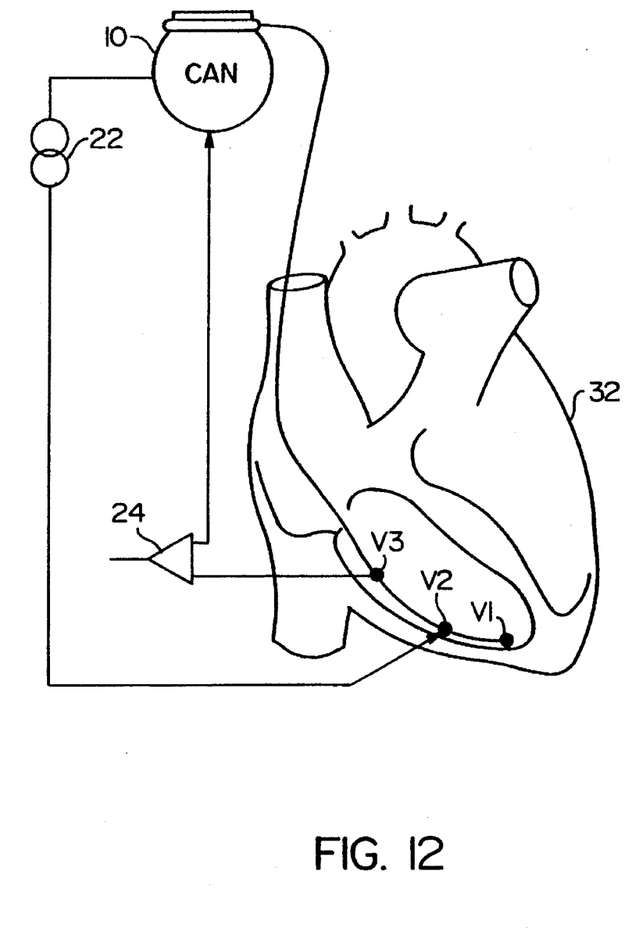
FIGS. 12 and 13 are diagrams illustrating two rheographic measurement configurations available with the lead configuration of FIG. 11.

During Time Slot 3-0, the canister serves as both source and recording electrode; ventricular electrode V3 serves as a recording electrode, and ventricular electrode V2 serves as a source electrode. The configuration of Time Slot 3-0, achieved by closing switches 18-1 and 18-9 along with switches 20-1 and 20-8, is depicted in FIG. 12. With the configuration of FIG. 12, transthoracic impedance is measured.

Figure 13:
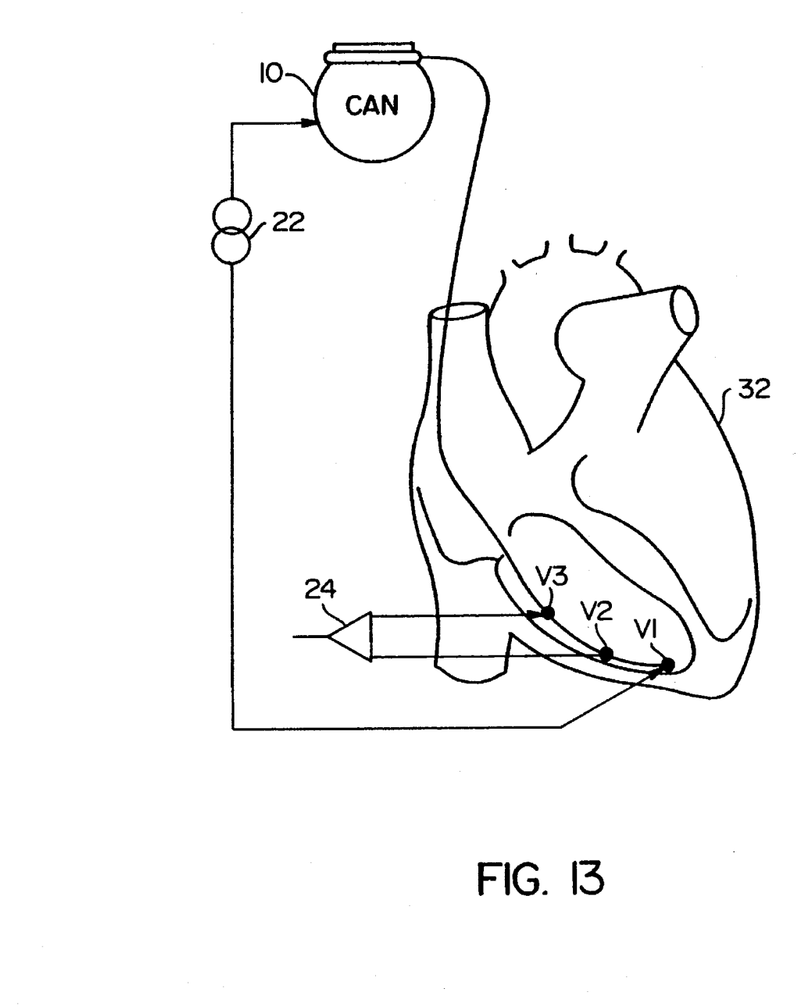

During Time Slot 3-1, the canister serves as a source electrode, electrodes V3 and V2 serve as recording electrodes, and electrode V1 serves as a source electrode. The configuration of Time Slot 3-1, achieved by closing switches 18-1 and 18-10 along with switches 20-3 and 20-9, is depicted in FIG. 13. With the configuration of FIG. 13, atrial intracardiac impedance is measured.

EXAMPLE NO. 4

Figure 14:
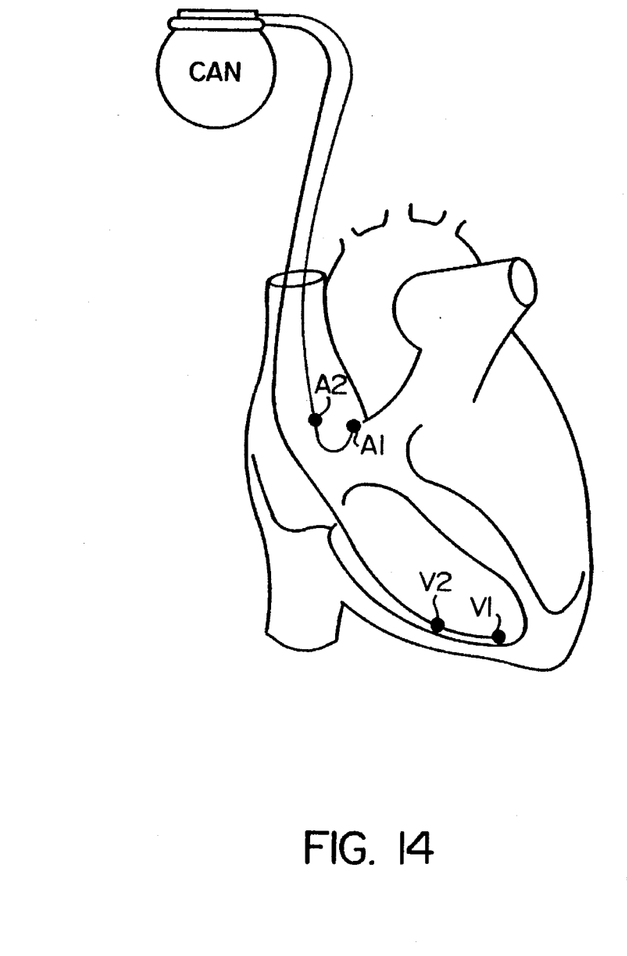
FIG. 14 is a diagram illustrating a fourth lead configuration for the pacemaker of FIG. 1.

In FIG. 14, there is shown a fourth example configuration for pacemaker 10 in accordance with the presently disclosed embodiment of the invention. The configuration of FIG. 14 utilizes two bipolar leads, one atrial and one ventricular. As would be appreciated by those of ordinary skill in the pacing art, this lead configuration is a conventional one for performing DDD pacing with bipolar atrial and ventricular sensing. With the configuration of FIG. 14, five-pole rheographic measurement is possible in four time slots. The configuration during each time slot is set forth in the following Table 7:

TABLE 7

|  | TIME SLOT 4-0 | TIME SLOT 4-1 | TIME SLOT 4-2 | TIME SLOT 4-3 |
|---|---|---|---|---|
| CAN | S/R | S/R | S | — |
| A2 | R | — | R | S |
| A1 | S | — | R | R |
| V2 | — | S | S | S |
| V1 | — | R | — | R |

In this fourth example configuration, the correspondence between lead conductors 16-1 and 16-5 in FIG. 2 and the electrodes is as set forth in the foregoing Table 2.

Figure 15:
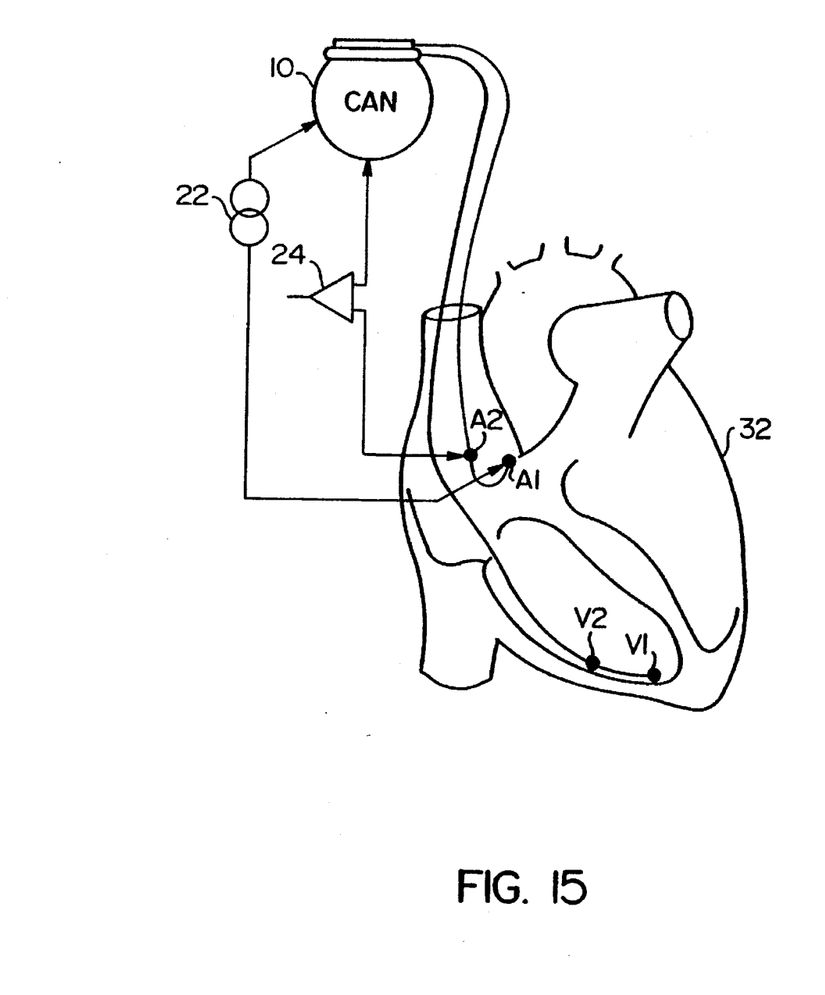
FIGS. 15, 16, 17, and 18 are diagrams illustrating four rheographic measurement configurations available with the lead configuration of FIG. 14.

During Time Slot 4-0, the canister serves as both a source and a recording electrode. Atrial electrode A2 serves as a recording electrode and electrode A1 serves as a source electrode. This configuration, achieved by closing switches 18-1 and 18-8 along with switches 20-1 and 20-7, is depicted in FIG. 15. With this configuration, transthoracic impedance is measured.

Figure 16:
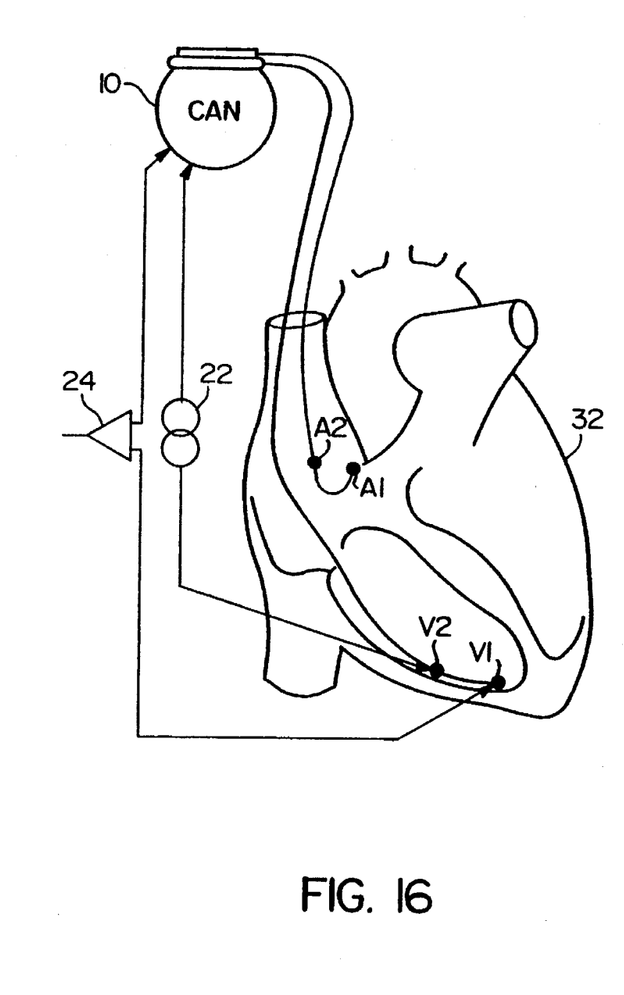

During Time Slot 4-1, the canister again serves as both a source and a recording electrode. Ventricular electrode V2 serves as a source electrode, while ventricular electrode V1 serves as a recording electrode. This configuration, achieved by closing switches 18-1 and 18-9 along with switches 20-1 and 20-10, is depicted in FIG. 16. With this configuration, transthoracic impedance is measured in the same manner as in the above-noted Telectronics Meta-MV device.

Figure 17:
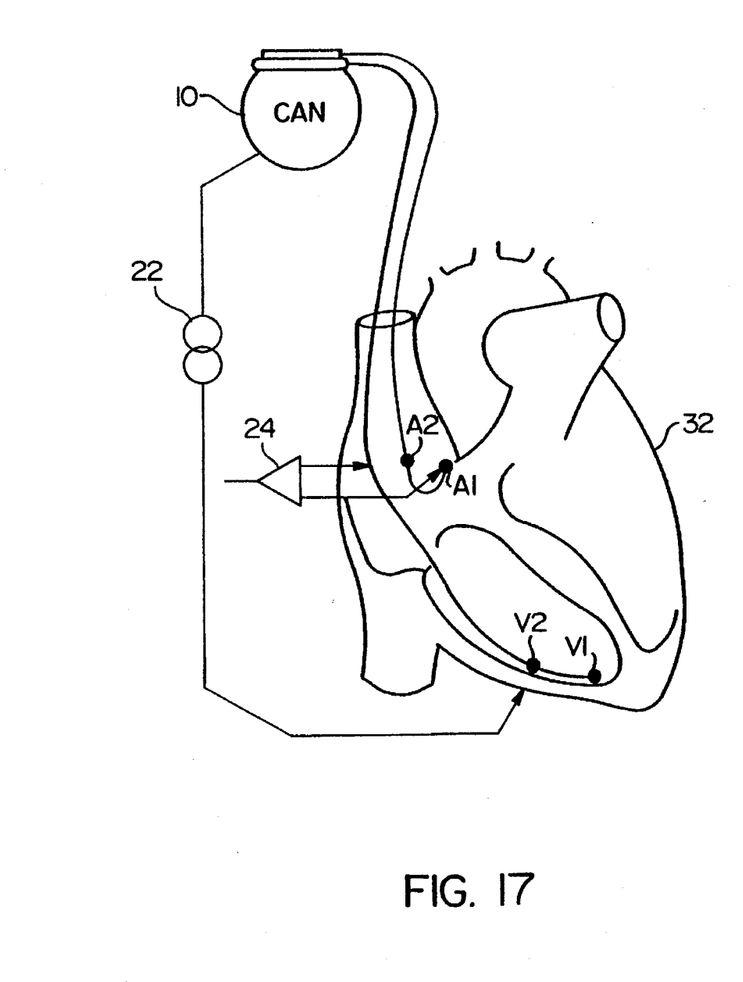

During Time Slot 4-2, the canister and ventricular electrode V2 serve as source electrodes, while electrodes A2 and A1 are recording electrodes. This configuration, achieved by closing switches 18-1 and 18-9 as well as switches 20-2 and 20-8, is depicted in FIG. 17. With this configuration, atrial intracardiac impedance is measured.

Figure 18:
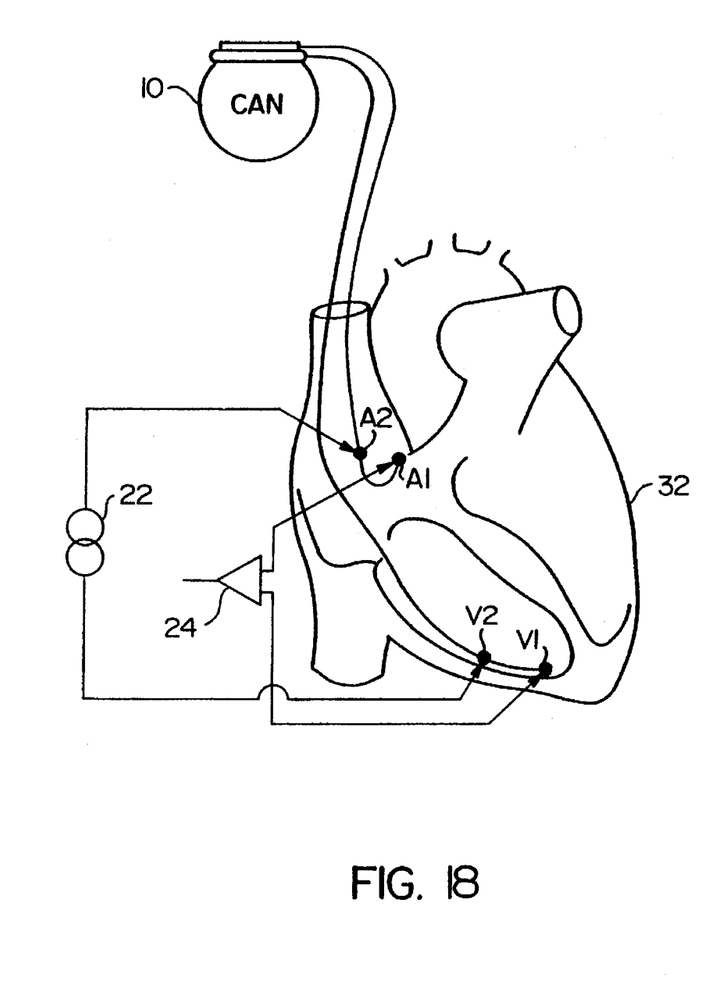

During Time Slot 4-3, electrodes A2 and V2 serve as source electrodes, while electrodes A1 and V1 serve as recording electrodes. This configuration, achieved by closing switches 18-2, 18-9, 20-3 and 20-10, is depicted in FIG. 18. With this configuration, ventricular intracardiac impedance is measured.

From the foregoing description, it should be apparent that pacemaker 10 in accordance with the presently disclosed embodiment of the invention is capable of dynamically reassigning the electrical function of the leads and electrodes coupled thereto, so that a plurality of rheographic measurement configurations can be realized. It should also be apparent that the present invention may be advantageously practiced in conjunction with any of the different types of pacemakers (VVI, VDD, DDD, etc . . .) and with any of the different types of standard pacemaker pace/sense leads (bipolar, tripolar, etc . . .). It is believed that, with the benefit of the present disclosure, those of ordinary skill in the pacemaker art would be able to readily adapt the present invention to be practiced with any number of lead conductors.

For a given pacemaker and lead combination, the present invention enables the pacemaker to perform a different rheographic measurement during each of a plurality of time slots defined in an appropriate rheography interval. The number of time slots can vary depending upon the number of electrodes and upon the desired rheographic configurations to be used.

Although a specific embodiment of the invention has been described herein in some detail, this has been done for the purposes of illustration only, and is not intended to be limiting with respect to the scope of the invention. It is contemplated that various substitutions, alterations, and/or modifications, including but not limited to those specifically discussed herein, may be made to the embodiment described herein without departing from the spirit and scope of the present invention as defined in the appended claims, which follow.

What is claimed is:

1. A pulse generator system comprising:

a plurality of electrodes, each adapted to be disposed at a separate site in a patient's body;

a plurality of conductive leads, each coupled at a distal end to one of said plurality of electrodes;

first and second switching circuits coupled to a proximal end of each of said plurality of leads;

a rheography pulse generating circuit coupled to said first switching circuit, said rheogmphy pulse generating circuit adapted to generate a constant current rheography pulse in response to a rheography pulse control signal;

an impedance detection circuit having first and second terminals coupled to said second switching circuit, said impedance detection circuit adapted to produce an output voltage corresponding to an impedance present between said first and second impedance detection circuit terminals;

control circuitry coupled to said first and second switching circuits and to said rheography pulse generating circuit. said control circuitry adapted to generate a source control signal identifying two of said plurality of leads, and to generate a recording control signal identifying two of said plurality of leads, and to generate said rheography pulse control signal;

wherein said first switching circuit is responsive to said source control signal to couple said two leads identified by said source control signal to said rheography pulse generating circuit, and wherein said second switching circuit is responsive to said recording control signal to couple said two leads identified by said recording control signal to said first and second impedance detection circuit terminals, respectively;

such that said rheography current pulse is conducted on said leads identified by said source control signal and such that said impedance detection circuit output voltage corresponds to impedance between said leads identified by said recording control signal.

2. A pulse generator system in accordance with claim 1 further comprising a conductive pacemaker canister coupled to said first and second switching circuits.

3. A method of detecting respiration and cardiac systole in a patient, comprising the steps of:

(a) implanting at least one multipolar pace/sense lead such that a plurality of pace/sense electrodes are disposed at spaced-apart in vivo sites;

(b) defining a plurality of time slots during which rheographic measurements are to be made;

(c) delivering a constant current pulse between different pairs of said electrodes during successive time slots; and (d) measuring the voltage differential between different pairs of said electrodes during successive time slots.

4. A cardiac pacemaker system, comprising:

a rheography pulse generating circuit adapted to generate constant current rheography pulses;

an impedance detection circuit having first and second terminals, said detection circuit adapted to generate an output voltage proportional to the voltage between said first and second terminals;

a plurality of electrodes adapted to be disposed at spaced apart in vivo sites;

a first switching circuit, coupled to said plurality of electrodes via a plurality of conductive leads and further coupled to said pulse generating circuit, said first switching circuit being responsive to source control signals identifying source conductor pairs from among said plurality of conductors to couple said source conductor pairs to said pulse generating circuit;

a second switching circuit, coupled to said plurality of electrodes via said plurality of conductive leads and further coupled to said impedance detection circuit, said second switching circuit being responsive to recording control signals identifying recording conductor pairs from among said plurality of conductors to couple said recording conductor pairs to said impedance detection circuit; and control circuitry coupled to said first and second switching circuit and to said pulse generating circuit, said control circuitry adapted to generate said source control signals and said record control signals.

5. A cardiac pacemaker system, comprising:

a rheography circuit including a rheography pulse generator, an impedance detector, and a switching circuit, said pulse generator adapted to generate a sequence of rheogmphy current pulses;

a plurality of electrodes adapted to be disposed at in vivo sites, coupled to said rheogmphy circuit by a plurality of pairs of conductive leads;

control circuitry, coupled to said switching circuit and to said pulse generator, said control circuitry adapted to control said switching circuit to couple a different pair of said conductive leads to said pulse generator for each one of said sequence of current pulses, and to couple a different pair of said conductive leads to said impedance detector for each of said sequence of current pulses.

6. A method of making rheographic measurements, comprising the steps of:

(a) disposing a plurality of electrodes at different in vivo sites;

(b) generating a series of rheography current pulses;

(c) for each rheography pulse generated in step (b), directing said pulses to a different pair of said electrodes; and (d) for each rheography pulse generated in step (b), coupling a different pair of said electrodes to an impedance detection circuit.

7. A cardiac pacemaker system, comprising:

a rheography circuit including a rheography pulse generator, an impedance detector, and a switching circuit, said pulse generator adapted to generate a rheography current pulse;

a first electrode adapted to be disposed in vivo, coupled to said rheography circuit by a first conductor;

a second electrode adapted to be disposed in vivo, coupled to said rheography circuit by a second conductor;

a third electrode adapted to be disposed in vivo, coupled to said rheography circuit by a third conductor;

control circuitry, coupled to said switching circuit and to said pulse generator, said control circuitry adapted to control said switching circuit to couple a different pair of said conductors to said pulse generator for each one of said rheography current pulses, and to couple a different pair of said conductors to said impedance detector for each of said rheography current pulses.

* * * * *